United States Patent
Geipel et al.

(10) Patent No.: US 11,288,805 B2
(45) Date of Patent: Mar. 29, 2022

(54) VERIFYING AND/OR IMPROVING THE CONSISTENCY OF LABELS WITHIN THE SCOPE OF MEDICAL IMAGE PROCESSING

(71) Applicant: Siemens Healthcare Diagnostics Inc., Tarrytown, NY (US)

(72) Inventors: Markus Michael Geipel, Munich (DE); Florian Büttner, Munich (DE); Gaby Marquardt, Hausen (DE); Daniela Seidel, Baiersdorf (DE); Christoph Tietz, Ottobrunn (DE)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 61 days.

(21) Appl. No.: 16/838,016

(22) Filed: Apr. 1, 2020

(65) Prior Publication Data

US 2020/0320709 A1   Oct. 8, 2020

(30) Foreign Application Priority Data

Apr. 2, 2019   (EP) ..................................... 19166679

(51) Int. Cl.
  *G06T 7/00*    (2017.01)
  *G06K 9/46*    (2006.01)
  *G06K 9/62*    (2022.01)

(52) U.S. Cl.
  CPC .............. *G06T 7/0016* (2013.01); *G06K 9/46* (2013.01); *G06K 9/6215* (2013.01); *G06K 9/6256* (2013.01); *G06T 2207/20072* (2013.01); *G06T 2207/20081* (2013.01); *G06T 2207/20084* (2013.01); *G06T 2207/30024* (2013.01)

(58) Field of Classification Search
None
See application file for complete search history.

(56) References Cited

U.S. PATENT DOCUMENTS

| | | | |
|---|---|---|---|
| 10,606,982 B2* | 3/2020 | Guo ...................... | G06F 40/169 |
| 10,650,520 B1* | 5/2020 | Beck ...................... | G06T 7/0012 |
| 11,080,855 B1* | 8/2021 | Beck ...................... | G06T 7/194 |
| 2011/0243417 A1 | 10/2011 | Madabhushi et al. | |
| 2012/0269436 A1 | 10/2012 | Mensink et al. | |

OTHER PUBLICATIONS

Extended European Search Report of EP Application No. 20162867.4 dated Oct. 14, 2020.

(Continued)

*Primary Examiner* — Leon Flores
(74) *Attorney, Agent, or Firm* — Dugan & Dugan, PC

(57) ABSTRACT

A computer-implemented method and a data processing apparatus provide and apply a trained probabilistic graphical model for verifying and/or improving the consistency of labels within the scope of medical image processing. Also provided are a computer-implemented method for verifying and/or improving the consistency of labels within the scope of medical imaging processing, a data processing apparatus embodied to verify and/or improve the consistency of labels within the scope of medical image processing, and a corresponding computer program product and a computer-readable medium.

16 Claims, 6 Drawing Sheets

(56) References Cited

OTHER PUBLICATIONS

Albayrak, Abdulkadir et al.: "Mitosis Detection Using Convolutional Neural Network Based Features" 2016 IEEE 17th International Symposium on Computational Intelligence and Informatics (CINTI), IEEE, Nov. 17, 2016 (Nov. 17, 2016), pp. 335-340, XP033060964, DOI: 10.1109 / CINTI.2016.7846429; the entire document, especially the abstract and Fig. 3.
Chen, Liang-Chieh et al.: "DeepLab: Semantic Image Segmentation with Deep Convolutional Nets, Atrous Convolution, and Fully Connected CRFs", ARXIV.org, Cornell University Library, 201 Olin Library Cornell University Ithaca, NY 14853, Jun. 2, 2016 (Jun. 2, 2016), XP080705599, the whole document, especially abstract and Fig. 1.
Chen, Yihua et al.: "Similarity-based Classification: Concepts and Algorithms", Journal of Machine Learning Research 10, Mar. 31, 2009 (Mar. 31, 2009), pp. 747-776, XP058264234, ISSN: 1532-4435; the whole document, especially the abstract and chapter "I Introduction".
Liu, An-An et al.: "A semi-Markov model for mitosis segmentation in time-lapse phase contrast microscopy image sequences of stem cell populations". IEEE Trans Med Imaging. Feb. 2012;31(2):359-69. doi: 10.1109/TMI.2011.2169495. Epub Sep. 26, 2011. PMID: 21954199.
Liu, Yiming et al.: "Automatic segmentation 11-18 of Cervical Nuclei Based on Deep Learning and a Conditional Random Field ", IEEE Access, vol. 6, Sep. 19, 2018 (Sep. 19, 2018), pp. 53709-53721, XP011692996, DOI: 10.1109/ ACCESS.2018.2871153; the whole document, in particular Abstract and Fig. 1.
Liu, Yushan et al.: "TIMELY: Improving Labeling Consistency in Medical Imaging for Cell Type Classification", ARXIV.org, Cornell University Library, 201 Olin Library Cornell University Ithaca, NY 14853, Jul. 10, 2020 (Jul. 10, 2020), XP081719307; the whole document.
Nie, Weizhi et al.: "Modeling Temporal Information of Mitotic for Mitotic Event Detection," in IEEE Transactions on Big Data, vol. 3, No. 4, pp. 458-469, Dec. 1, 2017, doi: 10.1109/TBDATA.2017.2723395.
Piccinini, Filippo et al.: "Advanced Cell Classifier: User-Friendly Machine-Learning-Based Software for Discovering Phenotypes in High-Content Imaging Data". Cell Syst. Jun. 28, 2017;4(6):651-655.e5. doi: 10.1016/j.cels.2017.05.012. Epub Jun. 21, 2017. PMID: 28647475.
Wu, Boqian et al : "Multi-scale deep neural network for mitosis detection in breast cancer histological images", Nov. 9, 2017 (Nov. 9, 2017), XP055623715, DOI: 10.20944 / preprints201711.0063.v1; found on internet on Sep. 19, 2019: https://www.preprints.org/manuscript/201711.0063/v1; Summary Chapter "3.1 Dataset "; Chapter "2.2 Multi-scale Fused Fully Convolutional Network"; Chapter "2.3 FF-CNN + CRF model".
Saez et al., "Handling Class Label Noise in Medical Pattern Classification Systems", Journal of Medical Informatics & Technologies, 24, pp. 123-130, ISSN 1642-6037; 2015.
Kondo et al., "Hidden Markov Tree Model for Word Alignment, Proceedings of the Eighth Workshop on Statistical Machine Translation", 2013, 503-511, Sofia, Bulgaria; 2013.
Albergante et al., "Robust and Scalable Learning of Complex Dataset Topologies via ElPiGraph", arXiv:1804.07580v2); 2018.
Reid et al., "Pseudotime Estimation: Deconfounding Single Cell Time Series", Bioinformatics, 32(19), 2016, 2973-2980.
Piccinini et al., "Advanced Cell Classifier: User-Friendly Machine-Learning-Based Software for Discovering Phenotypes in High-Content Imaging Data"; Cell Systems; vol. 4; No. 6; pp. 651-655.e5; XP055624626; ISSN: 2405-4712; DOI: 10.1016/j.cels.; 2017.05.012.

Northcutt et al., "Confident Learning: Estimating Uncertainty in Dataset Labels", arXiv:1911.00068v1; 2019.
Nie et al., "Modeling Temporal Information of Mitotic For Mitotic Event Detection"; IEEE Transactions On Big Data, IEEE; vol. 3; Mo.: 4; pp. 458-469; Xp11673467; Doi: 10.1109/TBDATA.2017.2723395; 2017.
Liu et al., "A Semi-Markov Model for Mitosis Segmentation in Time-Lapse Phase Contrast Microscopy Image Sequences of Stem Cell Populations"; IEEE Transactions On Medical Imaging, IEEE Service Center, Piscataway, NJ, US; vol. 31; No. 2; pp. 359-369; XP011491026; ISSN: 0278-0062; DOI: 10.1109/TMI.2011.2169495; 2011.
Albayrak et al., "Mitosis Detection Using Convolutional Neural Network Based Features"; 2016 IEEE 17th International Symposium On Computational Intelligence And Informatics; pp. 335-340; XP033060964; DOI: 10.1109/CINTI.2016.7846429; 2016.
Wu et al., "Multi-Scale Deep Neural Network for Mitosis Detection in Breast Cancer Histological Images"; Sep. 11, 2017; XP055623715 ; DOI10.20944/preprints201711.0063.v1; Gefunden im Internet: URL:https://www.preprints.org/manuscript/201711,0063/v1; 2017.
Sanchez et al., "On The Use of Neighbourhood-Based Non-Parametric Classifiers", Pattern Recognition Letters, 18, 11-13, 1179-1186; 1997.
Liu et al., "Automatic Segmentation of Cervical Nuclei Based on Deep Learning and a Conditional Random Field"; IEE Access; vol. 6; pp. 53709-53721; XP011692996; DOI: 10.1109/ACCESS.2018.2871153; 2018.
Koplowitz et al., "On the Relation of Performance to Editing in Nearest Neighbor Rules", 1981, Pattern Recognition, vol. 13, No. 3, pp. 251-255.
Haghverdi et al., "Diffusion Pseudotime Robustly Reconstructs Lineage Branching", Nature Methods, 13(10), 845-848); 2016.
Neal et al., "A View Of The EM Algorithm that Justifies Incremental, Sparse, and Other Variants", Learning In Graphical Models, p. 355-368; 1998.
Chen et al., "Single-cell Trajectories Reconstruction, Exploration and Mapping of Omics Data with STREAM", Nature Communications, 10, 1, 1903; 2019.
Coifman et al., "Diffusion Maps" Applied and Computational Harmonic Analysis 21, pp. 5-30; 2006.
Northcutt et al., "Learning with Confident Examples: Rank Pruning for Robust Classification with Noisy Labels" in Proceedings of the 33rd Conference on Uncertainty in Artificial Intelligence. AUAI Press; 2017.
Cannoodt, "SCORPIUS Improves Trajectory Inference and Identifies Novel Modules in Dendritic Cell Development", bioRxiv:10.1101/079509v2; 2016.
Chen et al., "Similarity-based Classification: Concepts and Algorithms"; Journal of Machine Learning Research, MIT Press, Cambridge, MA, US; vol. 10; pp. 747-776; XP058264234; ISSN: 1532-4435; 2009.
Chen et al., "DeepLab: Semantic Image Segmentation with Deep Convolutional Nets, Atrous Convolution, and Fully Connected CRFs"; Cornell University Library; XP080705599; arxiv.org; 2016.
Abkowitz et al., "Evidence that Hematopoiesis May Be a Stochastic Process In Vivo", Nature Medicine, vol. No. 2, 2, 190-197; 1996.
Saelens et al., "A Comparison Of Single-Cell Trajectory Inference Methods", Nature Biotechnology, 37,547-554; 2019.
Durand et al., "Computational Methods for Hidden Markov Tree Models—An Application to Wavelet Trees", IEEE Transactions on Signal Processing, vol. 52, No. 9, 2551-2560; 2004.
Van der Meer et al., "The Divergent Morphological Classification of Variant Lymphocytes in Blood Smears", JClinPathol, 60(7), 838-839; 2007.
Search Report of EP Application No. 19166679.1 dated Oct. 1, 2019.

* cited by examiner

VERIFYING AND/OR IMPROVING THE CONSISTENCY OF LABELS WITHIN THE SCOPE OF MEDICAL IMAGE PROCESSING

CROSS REFERENCE TO RELATED APPLICATION

This claims priority to European Patent Application No. EP 19166679.1, filed Apr. 2, 2019, which is hereby incorporated by reference herein in its entirety for all purposes.

FIELD

The present invention relates to labels within the scope of medical image processing.

BACKGROUND

The availability of labeled data is an important precondition for machine learning. Within the scope of medical image processing, labels are typically created by experts. This labeling approach is disadvantageous for a number of reasons: firstly, acquiring expert knowledge is a very time-consuming and work-intensive process, which only supplies satisfactory results after the many years of intensive practice. Furthermore, the method is prone to errors. Thus, the expert assessments may deviate by all means on account of a difference in experience or on account of different prior knowledge. Particularly in the case of the assessment of cell development lines, the labels often tend to correspond to an artificial categorization of a plurality of stages of continuous development. In this case, the experts sometimes set different borders between development stages or there may be a complete misclassification of the cells.

As may be gathered from the article van der Meer et al., 2007, J Clin Pathol, 60(7), 838-839, for example, there is a difference in opinion between the assessing experts in up to 10% of the samples. The document also mentions cases of conspicuous disagreement, with one cell being assigned to five different assessments in one case and more than 30% of the experts not being able to reproduce previous classifications.

Consequently, classifications created by experts are a relatively unreliable basis for a machine learning approach which is based on pattern recognition without plausibility control.

SUMMARY OF THE INVENTION

The present invention is therefore based on the object of providing a method that avoids false assessments or incorrect classifications of cells by experts, proposes corrections to assessments and provides feedback in respect of the plausibility of their assessment to persons skilled in the art of analyzing morphology.

This object is achieved by the subjects of the independent claims. The dependent claims reflect further advantageous aspects of the invention.

Moreover, the present invention relates to a computer-implemented method and a data processing apparatus for providing and applying a trained probabilistic graphical model for verifying and/or improving the consistency of labels within the scope of medical image processing, the use of the model for verifying and/or improving the consistency of labels within the scope of medical image processing, a computer-implemented method for verifying and/or improving the consistency of labels within the scope of medical imaging processing, a data processing apparatus embodied to verify and/or improve the consistency of labels within the scope of medical image processing, and a corresponding computer program product and a computer-readable medium.

Initially, the invention relates to a computer-implemented method for producing a trained probabilistic graphical model for verifying and/or improving the consistency of labels within the scope of medical image processing, the method including the following steps:

providing a set of images as training data, the images comprising image information of respectively one cell;

calculating a feature space for the training data, preferably with the aid of a deep convolutional neural network (DCNN), with an image corresponding to a feature vector in the feature space;

calculating the similarities between at least two data points of the training data on the basis of the feature space;

providing expert-generated labels for the cells, the images of which were provided as training data;

calculating hidden labels on the basis of the similarities between at least two data points of the training data and the expert-generated labels, preferably with the aid of a Viterbi algorithm; and producing a probabilistic graphical model for adapting the hidden labels, the probabilistic model preferably being a conditional random field (CRF) model.

This method is directed to unordered cells. Consequently, it relates to any cell type or any phenotypical characterization of cell features and does not presuppose that the cells to be analyzed are similar, for example, by virtue of having emerged from an inherent development line.

In an alternative approach, the present invention relates to a computer-implemented method for producing a trained probabilistic graphical model for verifying and/or improving the consistency of labels within the scope of medical image processing, wherein the cell can represent different development stages of a cell, comprising the following steps:

providing a set of images as training data, the images comprising image information of respectively one cell;

calculating a feature space for the training data, preferably with the aid of a deep convolutional neural network (DCNN), with an image corresponding to a feature vector in the feature space;

calculating the similarities between at least two data points of the training data on the basis of the feature space;

calculating a pseudotime, which orders the data points as per a development sequence;

providing expert-generated labels for the cells whose images were provided as training data;

calculating hidden labels on the basis of the development sequence reflected in the pseudotime and the expert-generated labels, preferably with the aid of a Viterbi algorithm; and producing a probabilistic graphical model for adapting the hidden labels, the probabilistic model preferably being a hidden Markov model (HMM) in the case of a linear development sequence and a hidden Markov tree (HMT) in the case of a dichotomous development sequence.

This method is directed to ordered cells. Consequently, it relates, in particular, to cells or phenotypical characterizations of cell features that are similar and typically emerge from an inherent development line.

In the center of the present application, the aforementioned preparatory computer-implemented methods are used as a basis for carrying out methods which provide an adaptation within the meaning of verification and/or improvement of the hidden labels on the basis of the probabilistic graphical model:

Thus, the present application particularly and advantageously relates to a computer-implemented method related to cells of a general type, wherein a probabilistic graphical model, preferably a probabilistic graphical model as obtained in the method described herein, is used for adapting hidden labels within the scope of medical image processing of cells. This method comprises the steps of:

providing hidden labels on the basis of the similarities between at least two data points of images as training data and expert-generated labels associated with this training data, the images comprising image information of respectively one cell;

linking the hidden labels and the expert-generated labels, the linking comprising a connecting of all hidden labels among themselves by means of undirected edges and a connecting of hidden labels and expert-generated labels by means of directed edges; and adapting or confirming the hidden labels on the basis of the probabilistic graphical model.

Thus, the present application furthermore and advantageously relates to a computer-implemented method related to cells of a development line, wherein a probabilistic graphical model, preferably a probabilistic graphical model as obtained in the method described herein, is used for adapting hidden labels within the scope of medical image processing of cells, which can represent different cell development stages. This method includes the steps of:

providing hidden labels on the basis of similarities between at least two data points of a set of images as training data, the images comprising image information of respectively one cell, and a pseudotime inferred therefrom, and expert-generated labels associated with the training data;

linking the hidden labels and the expert-generated labels, the linking comprising a connection of all labels by means of directed edges; and adapting or confirming the hidden labels on the basis of the probabilistic graphical model.

Adapting the hidden labels can be a correction of a previous assignment or classification of a cell, for example. This would be necessary if there is a discrepancy between the hidden label and the expert-generated labels. Alternatively, a previous assignment or classification of a cell can be confirmed. This would be the case where there is no discrepancy between the hidden label and the expert-generated labels, i.e., an identical or plausible classification is present.

Further details and specific configurations of the method can be gathered from the examples, which illustrate how it was possible to achieve a previously unachievable improvement in the labeling consistency with the aid of the method according to the invention.

One embodiment of calculating a feature space for the training dataset, as mentioned in the above-described methods, provides the use of a machine learning algorithm for this step. Within the context of this application, a machine learning algorithm is understood to mean, in particular, an algorithm embodied for machine learning. Typically, machine learning algorithms are subdivided into two classes: supervised learning algorithms and unsupervised learning algorithms. Supervised learning is the capability of AI (artificial intelligence) systems to reproduce laws, wherein the results are already present from observing nature or from expert decisions and are used to teach the system. Representative examples of supervised learning include the Bayes classifier, the naïve Bayes classifier, the nearest neighbor classification, the discriminant analysis, and artificial neural networks. In the case of supervised learning, use can typically be made of a function class that is based, for example, on decision trees, a random forest, a logistical regression, a support vector machine, network, a kernel process, or the like, or combinations thereof. Unsupervised learning denotes machine learning without the knowledge of target values known in advance. Here, attempts are made to identify patterns in the input data. Examples include automatic segmentation (clustering) and the compression of data for dimension reduction. By way of example, compression is implemented in principal component analysis. Furthermore, the machine learning algorithm can be embodied, for example, for deep learning and/or for reinforcement learning and/or for marginal space learning. Possible implementations of the machine learning algorithm can use artificial intelligence, for example. Optimization methods known to a person skilled in the art can be used for optimization purposes. Calculations, in particular during the optimization, can be carried out by means of a processor system, for example. By way of example, the processor system can have one or more graphics processors.

Particularly preferably, the features are calculated with the aid of a deep convolutional neural network (DCNN). A convolutional neural network is an artificial neural network that, as a matter of principle, consists of one or more convolutional layers, followed by a pooling layer. A DCNN, as is preferably used within the scope of the present invention, contains a plurality of repetitions of these layers. The convolutional layer typically comprises a two-dimensional or three-dimensional matrix. The activity of each neuron is calculated by way of a discrete convolution. A neuron in this layer reacts only to stimuli from its local surroundings. Information that is in principle superfluous is discarded in the pooling layer. An exemplary implementation of the pooling is max pooling, where only the activity of the most active neuron from each 2×2 square of neurons of the convolutional layer is maintained for the further computation steps. Following a few repeating units, consisting of convolutional and pooling layers, the network can be completed with one or more fully connected layers. The output of the last layer of the DCNN is typically converted into a probability distribution by way of a softmax function, i.e., a translation-invariant normalization over all neurons in the last layer.

For the purposes of calculating the similarities between two data points of the training data, use is made of a metric, a distance function or a kernel, for example. Here, at least the two data points are used as input values for obtaining a positive value as an output value, which describes the distance between the values, the similarity between the data points corresponding to a reciprocal value thereof. In certain embodiments, use can be made not only of the information from the specified two data points but also of information from other data points, preferably all other data points of the dataset for the purposes of calculating the similarities. An example of a typically employed kernel is:

$$K(x, x') = \exp\left(-\frac{\|x - x'\|^2}{2\sigma^2}\right)$$

Here, a similarity graph can advantageously be produced for the further determination of the similarities between two data points of the training data on the basis of the feature space, for example, two items of image data. Here, similarity groups are associated graphically. Typically, this method is not reliant on preliminary classification knowledge and is consequently free from being influenced by an incorrect classification.

Training data for the method may comprise images, with the images comprising image information of respectively one cell. Consequently, at least one set of images is provided as training data, the images comprising image information of respectively one cell. The corresponding information items can be available at different resolutions. The training data in the form of images and associated image information can likewise contain qualitative supplements. They may contain information in respect of the identity of the cells. This information could correspond to the expert-generated labels. In alternative embodiments, the expert-generated labels may be contained in a separate dataset. In this configuration, the image datasets or image information and labeling datasets or labeling information can be linked or otherwise referenced to one another. Moreover, the training data may comprise further data units, for example, information in respect of the recording unit used for the production thereof, information about the time of production, and optionally also patient information, geographical information or information in respect of the employed staining method or the like, should these have been carried out.

The expert-generated labels may contain information in respect of the cell type, an underlying disease, the status of the cells in respect of the cell division phase, for example, whether a cell is in a G, S, or M phase of the cell cycle. In this special embodiment, the labels would not reflect an inherent order or ordered assignment of the cells.

For use in methods for cell classification of cells of different development stages, these labels typically contain information in respect of the assessment or identification of the development stage of a cell. By way of example, the corresponding information can be available in the form of a class division or development division and consequently reflect an inherent order. Furthermore, the labels can contain information in respect of an already undertaken correction and/or a confirmation of the expert assessment.

In addition to the expert-generated labels, which are provided for the methods from external sources, there is a calculation of hidden labels as per the described methods. Such hidden labels reflect assessments of the cells in respect of the analyzed parameters and are based, in principle, on the feature comparison operations of the training data with image information in respect of the cells. The hidden labels can be associated with the corresponding expert-generated labels, i.e., the expert-generated labels available for the same cells. Here, it is likewise possible to register and store discrepancies between the labels.

Within the scope of using image data in respect of cells of different development stages that follow an inherent order, a pseudotime is calculated within the scope of the operations in the feature space. The pseudotime is a concept that was developed for transitions in biological systems. Here, individual cells are tracked during the transition from one stage to the next. Since cells typically do not run through this change of stages with a set frequency, there are variations in the time dimension. Here, the pseudotime is understood to mean a hidden dimension, i.e., a non-observed dimension, which describes the progress of the cells during the transition processes. Further information in this respect can be gathered, for example, from suitable literature citations, such as Reid and Wernisch, 2016, Bioinformatics, 32(19), 2973-2980.

Probabilistic graphical models (PGM), as obtained or used in the aforementioned methods, are generally graphs whose nodes are random variables and in which the absence of edges between these nodes indicates the independence thereof. Consequently, the PGMs provide a formalism that allows further probabilistic models to be presented or implemented.

A preferred embodiment of the method described herein, which is based on the evaluation of cells without inherent order, provides for the probabilistic model to be a conditional random field (CRF) model. A CRF is a type of undirected probabilistic model. Typically, it is used for segmenting sequences. By way of example, the CRF would receive a sequence x as input and output a sequence y of equal length. Here, the CRF can access the entirety of the information of the input sequence at each point, allowing the use of complex feature quantities.

Here, within the scope of using the CRF, linking of the calculated label and the expert-generated label is carried out on the basis of the conditional probability of the correctness of the expert-generated label. This can be implemented using various algorithms. By way of example, it is possible to resort to the loopy belief propagation algorithm, alpha expansion algorithm, mean field inference algorithm, or linear programming relaxation algorithm.

A preferred embodiment of the method described herein, which is based on the evaluation of cells with inherent order, provides for the use of hidden Markov concepts. By way of example, if the cells follow a linear development sequence, the probabilistic model is a hidden Markov model (HMM). If, by contrast, the cells follow a dichotomous development sequence, the probabilistic model is a hidden Markov tree (HMT).

An HMM is a stochastic model in which a system is modeled by a Markov chain with unobserved states. During the modeling as a Markov chain, the system typically randomly transitions from one state into another, with the transition probabilities only depending on the respective current state. Here, these states are not observed externally and are consequently hidden. Here, observable output symbols (emissions) are associated with each of these hidden states, the output symbols occurring with a certain probability depending on the state. An HMM can be used as a directed model for sequential data. Here, the HMM only accesses the current input, but not the entirety of the information of the input sequence.

A hidden Markov tree (HMT) is the development of the HMM, wherein the unobserved states depend on one another or follow one another in a tree structure. An example of how such an algorithm can be used can be gathered from the document Kondo et al., Proceedings of the Eighth Workshop on Statistical Machine Translation, 2013, 503-511, Sofia, Bulgaria. Here, an assumption is made that the alignment variables of the algorithm have a tree structure that is isomorphic to the target dependency tree. The algorithm models the probability of the distortion (distortion probability) on the basis of the source dependency tree.

Linking the calculated label and the expert-generated label on the basis of the conditional probability of the correctness of the expert-generated label is also carried out within the scope of using the HMM or the hidden Markov tree (HMT). Here, use is preferably made of the Viterbi algorithm.

The invention further relates to a data processing apparatus for producing a trained probabilistic graphical model for verifying and/or improving the consistency of labels within the scope of medical imaging, for example, proceeding from unordered cells, comprising:
- a unit for providing a set of images as training data, the images comprising image information of respectively one cell;
- a unit for calculating a feature space for the training data;
- a unit for calculating the similarities between at least two data points on the basis of the feature space;
- a unit for providing expert-generated labels for the cells, the images of which were provided as training data;
- a unit for calculating hidden labels on the basis of (i) the similarities between at least two data points or on the basis of the development sequence reflected in the pseudotime and (ii) the expert-generated labels; and
- a unit for producing a probabilistic graphical model for adapting the hidden labels.

The "adaptation" of the hidden labels can have, for example, the form of linking a label with the image, the linking comprising a correction or confirmation of the already available expert-generated label for this image, i.e., a verification and/or improvement of this expert-generated label, and outputting and/or storing the image together with the corrected or confirmed linked label.

The invention further relates to data processing apparatus for producing a trained probabilistic graphical model for verifying and/or improving the consistency of labels within the scope of medical imaging of cells, which, e.g., represent different development stages of a cell and are consequently subject to an inherent order, comprising:
- a unit for providing a set of images as training data, the images comprising image information of respectively one cell;
- a unit for calculating a feature space for the training data;
- a unit for calculating the similarities between at least two data points on the basis of the feature space;
- a unit for calculating a pseudotime, which orders the data points as per a development sequence;
- a unit for providing expert-generated labels for the cells, the images of which were provided as training data;
- a unit for calculating hidden labels on the basis of (i) the development sequence reflected in the pseudotime and (ii) the expert-generated labels; and
- a unit for producing a probabilistic graphical model for adapting the hidden labels.

Furthermore, the invention provides a developed data processing apparatus, which can be used for adapting hidden labels within the scope of medical image processing of cells, for example, unordered cells, on the basis of a trained probabilistic graphical model, wherein the data processing apparatus comprises:
- a unit for providing hidden labels on the basis of the similarities between at least two data points of a set of images as training data and expert-generated labels associated with this training data, the images comprising image information of respectively one cell;
- a unit for linking the hidden labels and the expert-generated labels, the linking comprising a connecting of all hidden labels among themselves by means of undirected edges and a connecting of hidden labels and expert-generated labels by means of directed edges; and
- a unit for receiving adapted hidden labels on the basis of the probabilistic graphical model.

Furthermore, the invention provides for a further developed data processing apparatus, which can be used for adapting hidden labels within the scope of medical image processing of cells, which, for example, represent different development stages of a cell and are consequently subject to an inherent order, on the basis of a trained probabilistic graphical model, wherein the data processing apparatus comprises:
- a unit for providing hidden labels on the basis of similarities between at least two data points of a set of images as training data, the images comprising image information of respectively one cell, and a pseudotime inferred therefrom, and expert-generated labels associated with the training data;
- a unit for linking the hidden labels and the expert-generated labels, the linking comprising a connection of all labels by means of directed edges; and
- a unit for receiving adapted hidden labels on the basis of the probabilistic graphical model.

The invention further relates, in particular, to the use of a trained probabilistic graphical model, which was provided as per a method for producing a trained probabilistic graphical model according to one or more aspects of this invention, for verifying and/or improving the consistency of labels within the scope of medical imaging of cells.

The probabilistic models obtained uncover in the process discrepancies between the computed hidden labels and the expert-generated labels which (i) suggests checking the expert-generated labels or the analysis method by the experts or (ii) leads to the expert-generated labels being corrected and thus increasing the classification homogeneity or cell assessment.

In particular, the trained probabilistic graphical model is used to correct an expert-generated label of image information on the basis of a derived hidden label or to confirm it.

Preferably, a probabilistic graphical model trained according to the invention, as described herein, is used to correct or confirm, on the basis of an inferred hidden label, an expert-generated label of image information. The use of probabilistic graphical models as described herein for verifying and possibly improving the consistency of labels within the scope of medical image processing is particularly advantageous since this facilitates reworking or an improvement of expert-generated labels and thus, independently of found discrepancies in the assessment, can be provided for a renewed check by experts. This procedure can be repeated one or more times such that a further optimization and increase in consistency is implementable.

The invention further relates to a computer-implemented method for verifying and/or improving the consistency of labels within the scope of medical image processing, including the steps of:
- providing an image of a cell;
- providing an available expert-generated label;
- calculating a feature space for the image;
- applying a method on the basis of the trained probabilistic graphical model on the calculated features of the image;
- linking a label with the image, the linking comprising a correction or confirmation of the already available expert-generated label for this image; and
- outputting and/or storing the image together with the corrected or confirmed linked label.

In one embodiment of the invention, the trained probabilistic graphical models used in the specified computer-implemented method are those that were described above. In addition or as an alternative thereto, the methods to be applied can be those that were described above.

In a specific embodiment, the invention relates to a computer-implemented method for verifying and/or improving the consistency of labels within the scope of medical image processing, including the steps of:
providing the image of a cell;
providing an available expert-generated label;
using background information in respect of the image of the cell to define the topology of a hidden Markov tree (HMT), a start probability and an emission matrix;
learning the feature representations of the image using a neural network;
choosing a suitable pseudotime inference algorithm and calculating pseudotimes on the basis of the feature vectors;
sorting the expert-generated labels according to increasing pseudotime;
configuring a hidden Markov tree (HMT), in which the sorted expert-generated labels are the observed information;
learning the parameters of transition matrices using the generalized EM algorithm;
applying the generalized Viterbi algorithm in order to infer the most probable true labels;
identifying images with inconsistent labels by virtue of comparing the actual labels with the expert-generated labels; and
outputting images with inconsistent labels, which additionally contain proposed labels.

Further details and definitions in respect of this method can be gathered from examples 1 to 4, in particular example 4.

In a further embodiment of the invention, the computer-implemented method, as described above, is supplemented by a correction of an already available expert-generated label leading to a feedback query with an expert in respect of the labeling discrepancy. Firstly, this forwards a plausibility warning to the expert in respect of their assessment. At the same time, the generation of feedback, possibly after reevaluation of the assessment by the expert or group of experts, may lead to an improvement in the employed model or to an improvement of an inferred automated classification approach.

In a further, particularly preferred embodiment, the computer-implemented method for verifying and/or improving the consistency of labels within the scope of medical imaging, which includes the steps of:
providing the image of a cell;
providing an available expert-generated label;
calculating a feature space for the image;
applying a method on the basis of a trained probabilistic graphical model on the calculated features of the image;
linking a label to the image, the linking comprising a correction or confirmation of the already available expert-generated label for this image; and
outputting and/or storing the image together with the corrected or confirmed linked label,
is run through again, at least once or multiple times.

In a further embodiment, one or more images that have not been analyzed previously are compared to an already calculated feature space, as described herein, and a trained probabilistic graphical model, as described herein, in order to infer labels in the case of correspondence which are preferably used in the already calculated transition borders within the feature space.

Furthermore, the invention relates to a data processing apparatus, embodied to verify and/or improve the consistency of labels within the scope of medical image processing, wherein the apparatus has at least one processor and a memory, wherein the at least one processor is configured to load and execute program code from the memory and, on the basis of the execution of the program code, carry out the following steps:
providing the image of a cell;
providing an available expert-generated label;
calculating a feature space for the image;
applying a method on the basis of a trained probabilistic graphical model on the calculated features of the image;
linking a label to the image, the linking comprising a correction or confirmation of the already available expert-generated label for this image; and
outputting and/or storing the image together with the corrected or confirmed linked label.

In one embodiment of the invention, the steps to be carried out in the specified data processing apparatus are specified in that the trained probabilistic graphical models mentioned are those that were described above. In addition or as an alternative thereto, the specified methods to be used can be those methods that were described above.

The data processing apparatus as described herein and/or one or more components thereof can be formed by a data processing system. By way of example, the data processing system can have one or more components in the form of hardware and/or one or more components in the form of software.

By way of example, the data processing system can be formed at least in part by a cloud computing system. By way of example, the data processing system can be and/or have a cloud computing system, a computer network, a computer, a tablet computer, a smartphone or the like, or a combination thereof.

By way of example, the hardware can interact with software and/or can be configurable by means of software. By way of example, the software can be executed by means of the hardware. By way of example, the hardware can be a memory system, an FPGA (field-programmable gate array) system, an ASIC (application-specific integrated circuit) system, a microcontroller system, a processor system, and combinations thereof. By way of example, the processor system can have a microprocessor and/or a plurality of cooperating microprocessors. In particular, a component of the data processing apparatus according to one of the aspects disclosed in this application, which is embodied to carry out a given step of a method according to one of the aspects disclosed in this application, can be implemented in the form of hardware that is configured to carry out the given step and/or that is configured to carry out a computer-readable instruction in such a way that the hardware is configurable by means of the computer-readable instruction to carry out the given step. In particular, the system can have a storage region, for example, in the form of a computer-readable medium, in which computer-readable instructions, for example, in the form of a computer program, are stored.

A data transfer between components of the data processing system can be respectively implemented, for example, by means of a suitable data transfer interface. The data transfer interface for data transfer to and/or from a component of the data processing system can be realized at least partly in the form of software and/or at least partly in the form of hardware. By way of example, the data transfer interface can be embodied to store data in and/or to load data from a region of the memory system, wherein one or more components of the data processing system are able to access this region of the memory system.

The invention furthermore relates to a computer program product with a computer program, which is directly loadable into a memory device of a computer, comprising program sections for carrying out all steps of a method according to one or more of the aspects specified herein when the computer program is executed on the computer.

The computer program is loadable into the memory system of the data processing system and executable by the processor system of the data processing system. By way of example, the data processing system can be embodied by means of the computer program in such a way that the data processing system can carry out the steps of a method according to one of the embodiments specified in this application when the computer program is executed by the data processing system.

By way of example, the computer program product can be the computer program or comprise at least one additional constituent part in addition to the computer program. The at least one additional constituent part of the computer program product can be embodied as hardware and/or as software. By way of example, the computer program product can have a storage medium on which at least some of the computer program product is stored and/or a key for authenticating a user of the computer program product, in particular in the form of a dongle.

The computer program product and/or the computer program can have, for example, a cloud application program, which is embodied to distribute program sections of the computer program among different processing units, in particular different computers, of a cloud computing system, wherein each of the processing units is embodied to execute one or more program sections of the computer program.

The invention furthermore relates to a computer-readable medium, on which program sections that are readable and executable by a computer are stored in order to carry out all steps of a method according to one or more of the aspects specified herein when the program sections are executed by the computer.

By way of example, the computer program product according to one of the embodiments disclosed in this application and/or the computer program according to one of the embodiments disclosed in this application can be stored on the computer-readable medium.

By way of example, the computer-readable medium can be a memory stick, a hard disk drive, or any other data medium which can be connected, in particular, detachably connected, to the data processing system or can be securely integrated in the data processing system. By way of example, the computer-readable medium can form a region of the memory system of the data processing system.

Consequently, in a secondary aspect, the solution according to the invention within the context of the above-described aspects facilitates the improvement of a general classification method for cell assignment or cell classification, likewise contained herein, which is based on a simple machine learning algorithm without plausibility control. Here, there is an increase in the data quality, in particular, so that a more accurate, and hence also more cost-efficient, automatic classification is implemented. Moreover, some of the subjects according to the invention specified herein allow more consistent and reproducible borders to be set between cell development stages. In the process, the expert-generated labels are consolidated and consequently become usable more broadly. Furthermore, the generation of feedback, as explained above, can contribute to the creation of new guidelines or rules for manual assessment. Moreover, the solution according to the invention can also lead to an improvement of the dialogue between the expert and a machine-learning engineer, contributing to an improvement in the data consistency.

Within the scope of the inventions, features that are described in relation to different embodiments of the invention and/or different claim categories (method, use, apparatus, etc.) can be combined to form further embodiments of the invention. By way of example, a claim relating to an apparatus can also be developed using features described or claimed in conjunction with a method, and vice versa. Functional features of a method can be configured by appropriately embodied physical components in the process. In addition to the embodiments of the invention explicitly described in this application, multifaceted further embodiments of the invention are conceivable; a person skilled in the art can arrive at these without departing from the scope of the invention as defined by the claims.

The use of the indefinite article "a" or "an" does not preclude the relevant feature from being present multiple times as well. The use of the expression "to have" does not preclude terms linked by means of the expression "to have" from being able to be identical. The use of the expression "unit" does not preclude the object to which the expression "unit" relates from being able to have a plurality of components that are spatially separated from one another. In the context of the present application, the expression "based on" or "on the basis of" can be understood in particular to mean within the meaning of the expression "using". In particular, phrasing according to which a first feature is produced (alternatively: ascertained, determined, etc.) on the basis of a second feature does not preclude the first feature from being able to be produced (alternatively: ascertained, determined, etc.) on the basis of a third feature.

Below, the invention will be explained on the basis of further exemplary embodiments with reference to the attached figures. The illustration in the figures is schematic, greatly simplified and not necessarily true to scale.

DETAILED DESCRIPTION OF THE INVENTION

Figure 1:
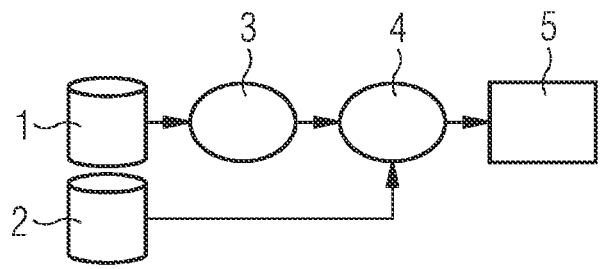
FIG. 1 shows the state of the art of the machine learning process from the prior art.

FIG. 1 shows the state of the art of the machine learning process from the prior art. Here, a feature calculation 3 is carried out using image data 1. The results are supplied to a module for machine learning 4. This module is likewise supplied with expert-generated labels 2. A classification model 5 can be created after running through a machine learning process 4.

Figure 2:
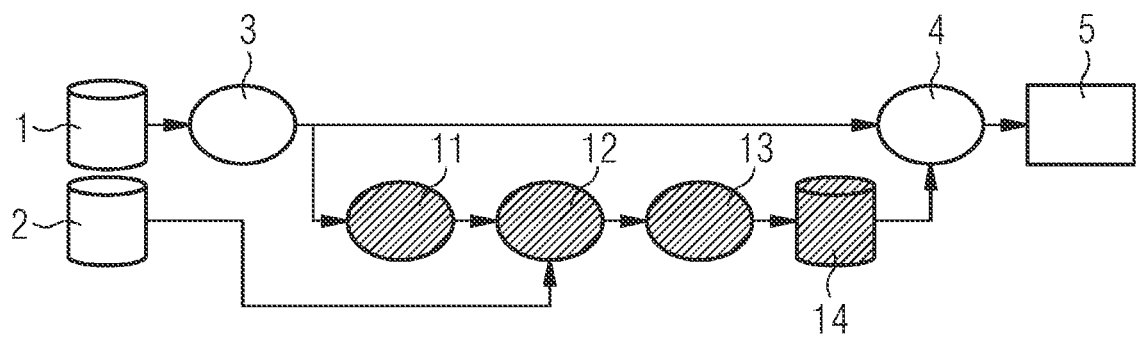
FIG. 2 shows a schematic calculation method on the basis of unordered cells.

FIG. 2 shows a schematic calculation method according to the invention, which is based on unordered cells or arbitrary classes. Here, a feature calculation 3 is initially carried out using image data 1. While the previous methods have directly supplied the results of this calculation to a model for machine learning 4, the invention is based on establishing a label correction subsystem (11, 12, 13 and 14). Here, a similarity graph 11 is calculated first. A probabilistic model in the form of a conditional random field (CRF) 12 is created in a next step. This model is likewise fed with expert-generated labels 2.

Subsequently, hidden labels 13 can be inferred after the application of the CRF. This leads to possible correction of the hidden labels 14. These are then supplied to a module for machine learning 4, which can finally generate a classification model 5.

Figure 3:
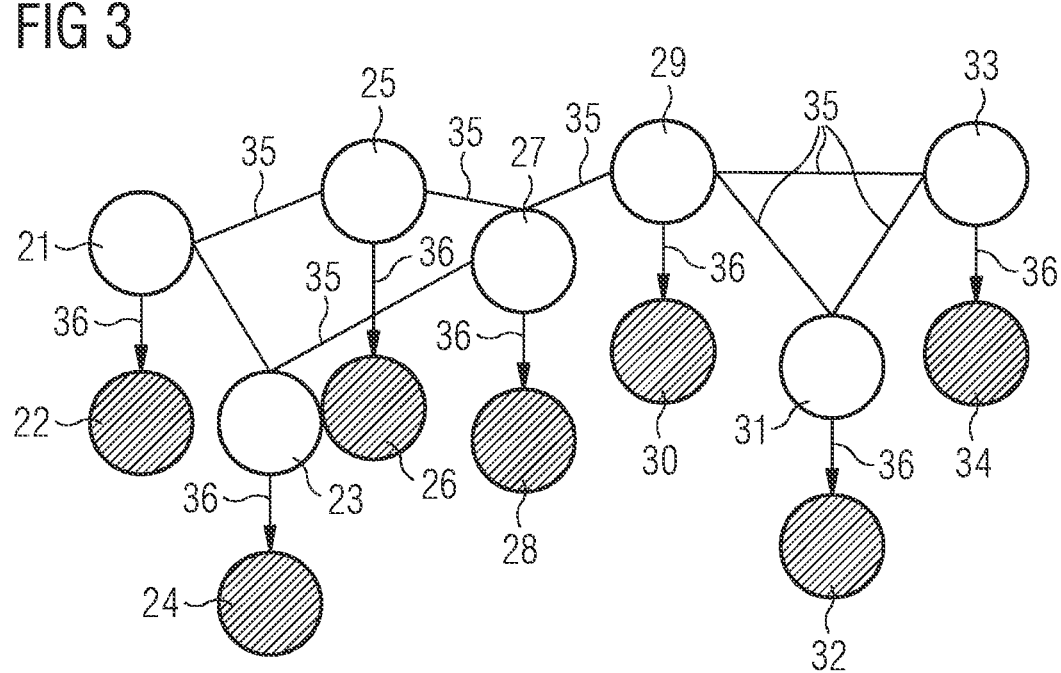
FIG. 3 shows the linking of labels for unordered cells.

FIG. 3 schematically shows the linking of the labels for unordered cells. Here, a hidden label of cell A 21 is linked to an expert-generated label of cell A 22, a hidden label of cell B 23 is linked to an expert-generated label of cell B 24, a hidden label of cell C 25 is linked to an expert-generated label of cell C 26, a hidden label of cell D 27 is linked to an expert-generated label of cell D 28, a hidden label of cell E 29 is linked to an expert-generated label of cell E 30, a hidden label of cell F 31 is linked to an expert-generated label of cell F 32, and a hidden label of cell G 33 is linked to an expert-generated label of cell G 34 by means of directed edges 36. Linking of the hidden labels among themselves is provided by means of undirected edges 35.

Figure 4:
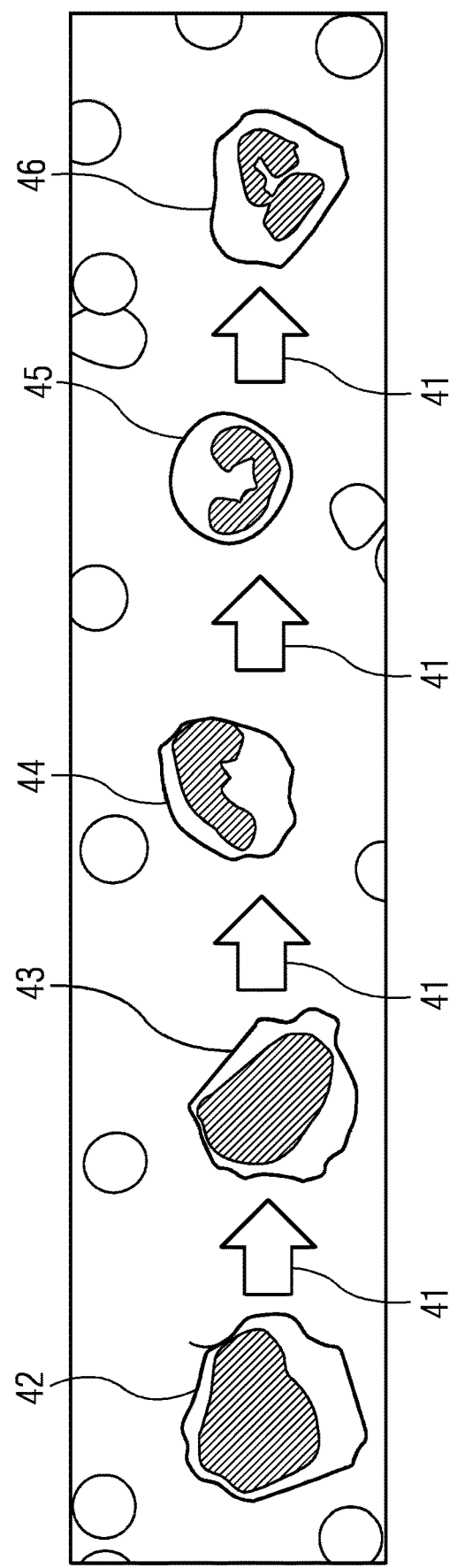
FIG. 4 shows the development stages of a granulocyte. The stages myeloblast, promyelocyte, myelocyte, metamyelocyte, and band segmented neutrophil are illustrated from left to right.

FIG. 4 shows a transition between various cell development stages 41 using the example of granulocytes. From left to right, the myeloblast 42, promyelocyte 43, myelocyte 44, metamyelocyte 45, and band segmented neutrophil 46 stages are illustrated.

The imaged cells correspond to an ordered sequence and differ from arbitrary classes by inherent ordering principles, such as similar structure or similar size, but differ in terms of the morphology of the cell nucleus, etc.

Figure 5:
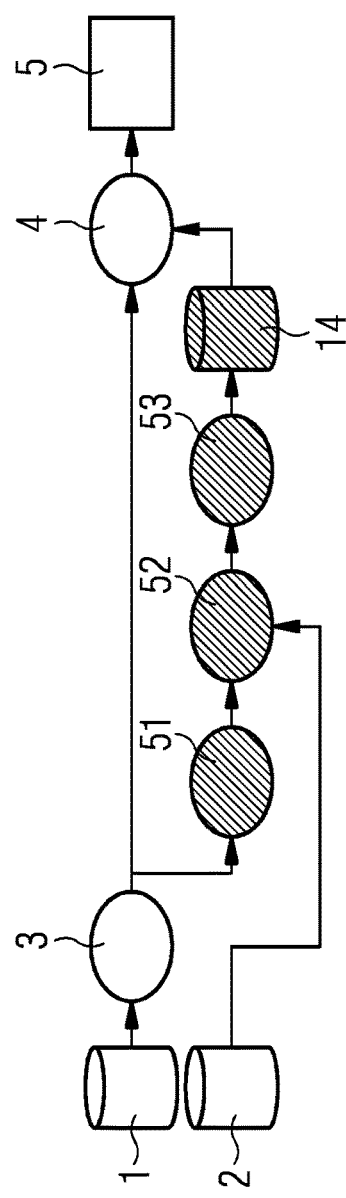
FIG. 5 shows a schematic calculation method for cells that are subject to a transition of cell development stages.

FIG. 5 shows a schematic calculation method according to the invention on the basis of cells that are subject to a transition of cell development stages. Here, a feature calculation 3 is initially carried out using image data 1. While the previous methods have directly supplied the results of this calculation to a module for machine learning 4, the invention is based on establishing a label correction subsystem (51, 52, 53 and 14). Here, a pseudotime 51 is calculated first. A probabilistic model in the form of a hidden Markov model (HMM) 52 is created in the next step. This model is likewise fed with expert-generated labels 2.

Subsequently, labeling borders can be inferred in pseudotime 53 following the application of the HMM. This leads to possible correction of the hidden labels 14. These are then supplied to a module for machine learning 4, which can finally generate a classification model 5.

Figure 6:
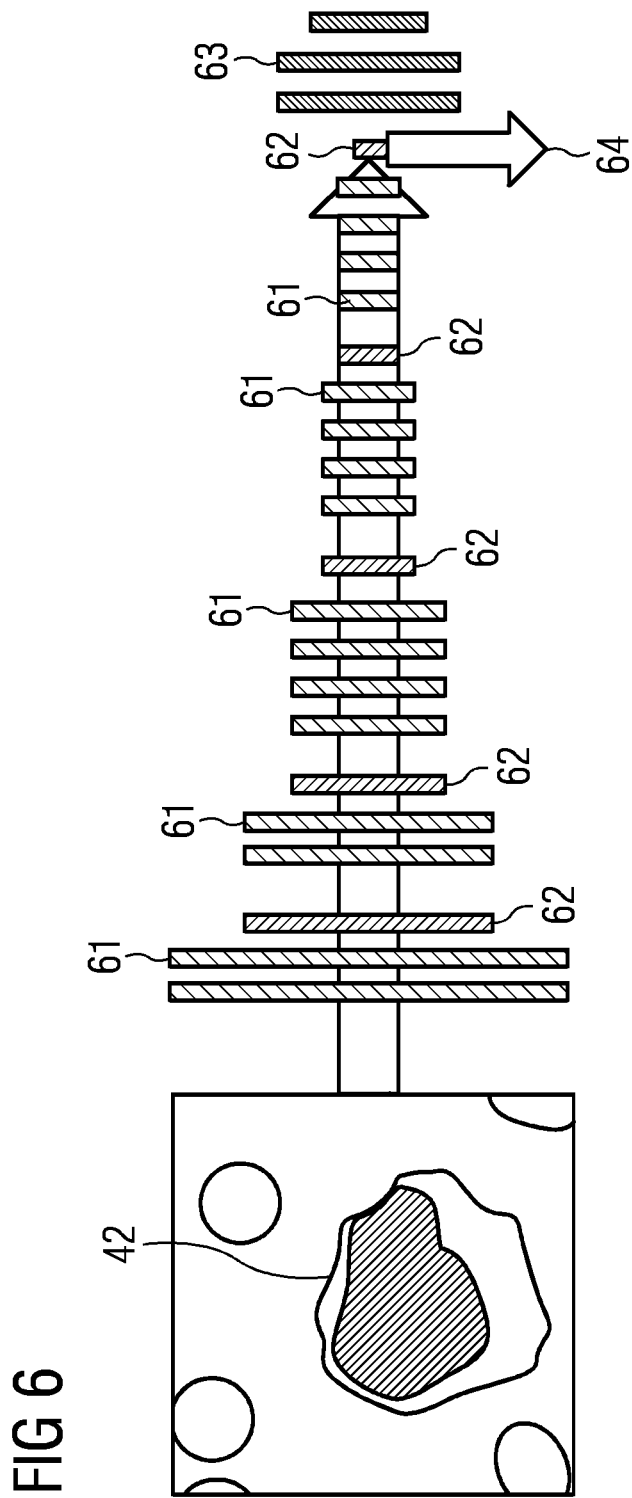
FIG. 6 shows a deep convolutional neural network for calculating a feature space for the training datasets.

FIG. 6 shows a deep convolutional neural network (DCNN) for calculating a feature space for training datasets. Starting point is the image of a myeloblast 42 as a training dataset, the features of which are analyzed by means of a neural network by convolution 61, max pooling 62, and compression 63 in order to obtain a representation in the feature space 64.

Figure 7:
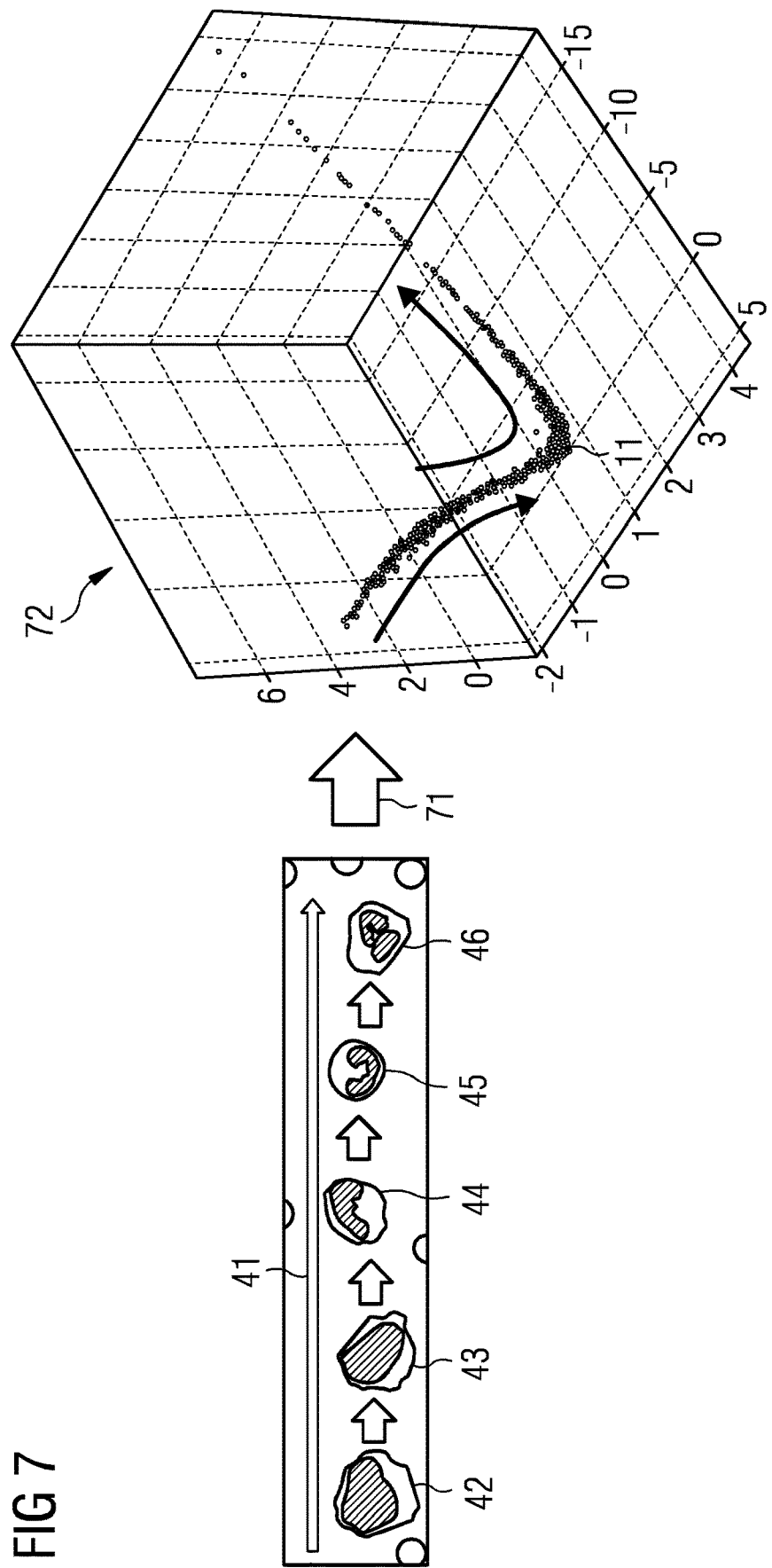
FIG. 7 shows the representation of cells in the feature space. The inferred information items in respect of the cells are disposed in the form of a similarity graph, the curve extending in relation to the development stage of the cells.

FIG. 7 shows the representation of cells in the feature space. In the left image region, it is possible to identify the transition between different cell development stages 41 using the example of granulocytes. From left to right, the myeloblast 42, promyelocyte 43, myelocyte 44, metamyelocyte 45, and band segmented neutrophil 46 stages are illustrated. Following a transformation 71, a feature space 72 is created, which can be represented in the form of a similarity graph 11. The inferred information items in respect of the cells are disposed here in the form of the similarity graph 11, wherein the curve is disposed in relation to the development stage of the cells.

Figure 8:
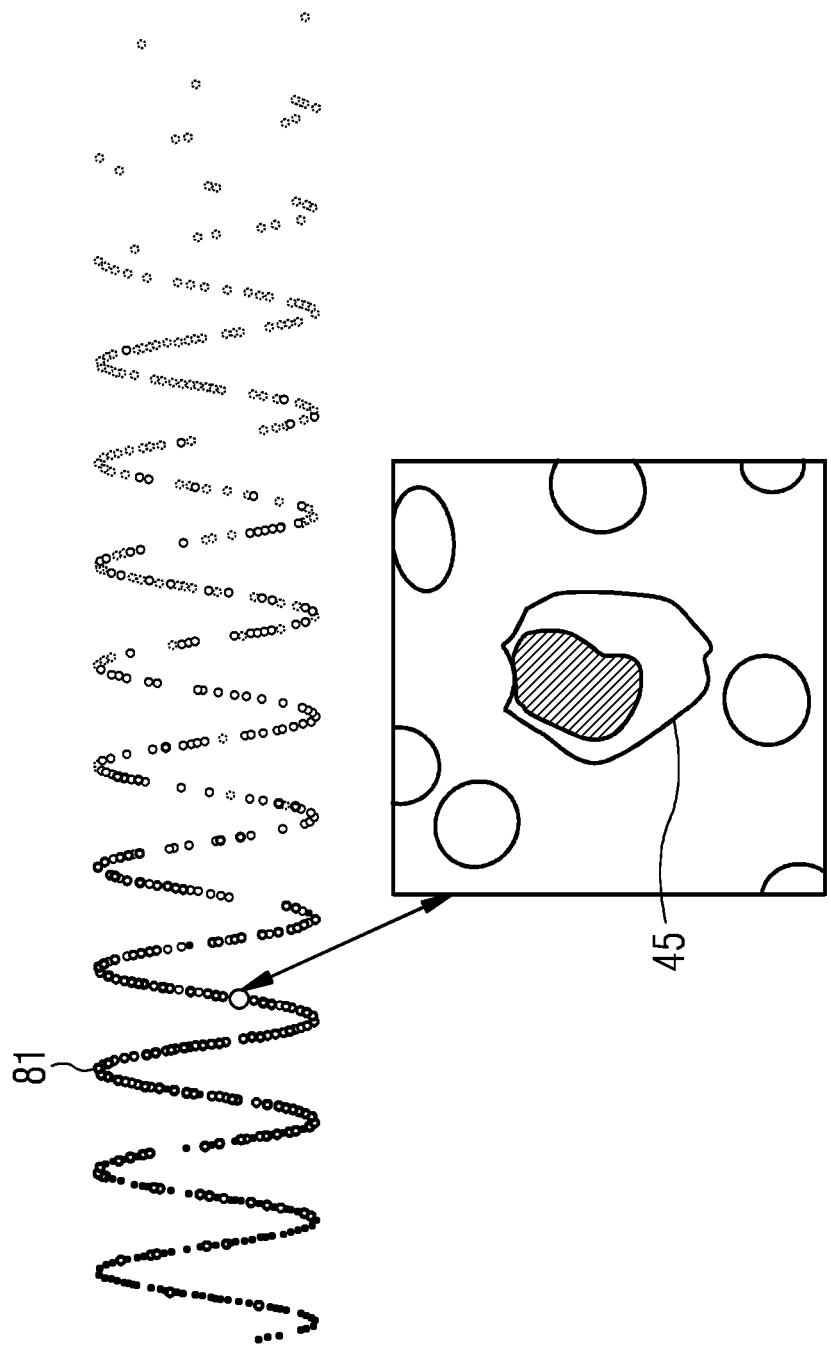
FIG. 8 shows the sequence of cells in pseudotime, wherein a link can be established between the pseudotime and the representation according to the image data.

FIG. 8 reflects the sequence of cells in pseudotime 81, wherein a link can be established between the pseudotime and the representation as per the image data. As an example, the positioning of a metamyelocyte 45 is illustrated.

Figure 9:
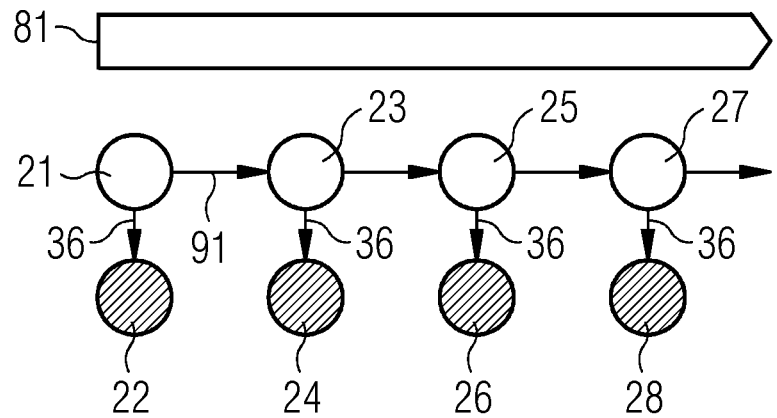
FIG. 9 shows the link between hidden labels and expert-generated labels as an initial situation for the application of a hidden Markov model.

FIG. 9 shows the link of hidden labels and expert-generated labels as an initial situation for the application of a hidden Markov model within the scope of the analysis of cells which are subject to transition between different cell development stages, i.e., which are not unordered. These are initially arranged within the scope of the calculated pseudotime 81. Subsequently, the hidden label of cell A 21 is linked to an expert-generated label of cell A 22, a hidden label of cell B 23 is linked to an expert-generated label of cell B 24, a hidden label of cell C 25 is linked to an expert-generated label of cell C 26, and a hidden label of cell D 27 is linked to an expert-generated label of cell D 28. The distance between the cells within the scope of the pseudotime concept is shown as the distance to the next cell in pseudotime 91. The hidden labels and the expert-generated labels are linked by means of directed edges 36.

Figure 10:
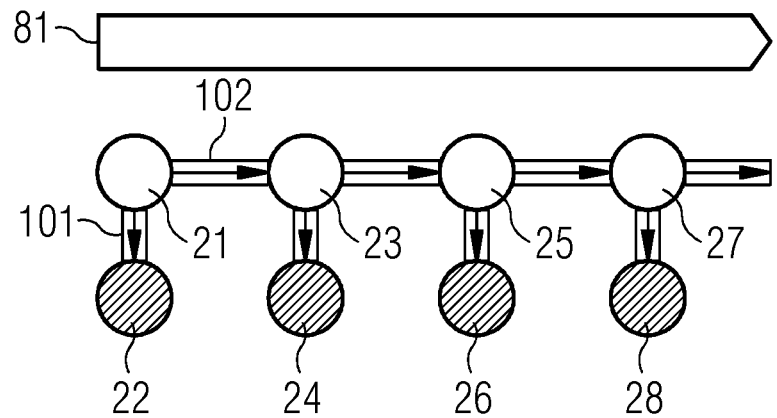
FIG. 10 shows the link between hidden Labels and expert-generated labels following the application of a hidden Markov model.

FIG. 10 shows a link of hidden labels and expert-generated labels following the application of a hidden Markov model within the scope of the analysis of cells which are subject to transition between different cell development stages, i.e., which are not unordered. These are initially arranged within the scope of the calculated pseudotime 81. Subsequently, the hidden label of cell A 21 is linked to an expert-generated label of cell A 22, a hidden label of cell B 23 is linked to an expert-generated label of cell B 24, a hidden label of cell C 25 is linked to an expert-generated label of cell C 26, and a hidden label of cell D 27 is linked to an expert-generated label of cell D 28. Here, there is coding of the links by the transition matrix of the HMM 102 and coding in the emission probability of the HMM 101. The hidden labels and the expert-generated labels are linked by means of directed edges 36.

Figure 11:
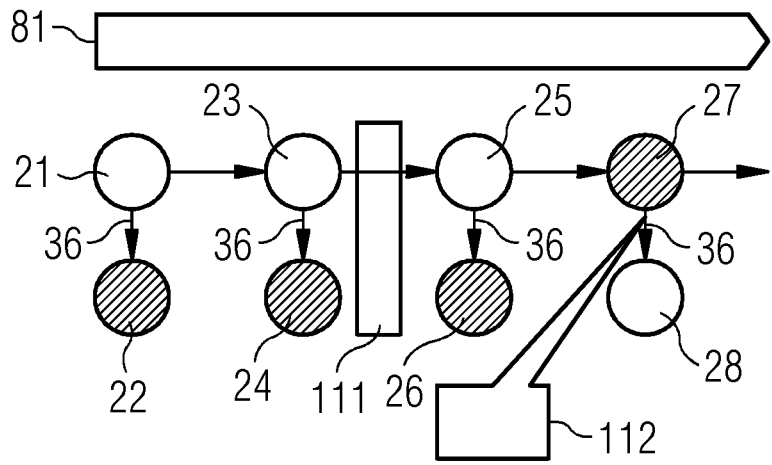
FIG. 11 shows discrepancies between the hidden labels and the expert-generated labels, which could lead to incorrect assessments being uncovered.

FIG. 11 shows discrepancies between the hidden labels and the expert-generated labels, which could lead to incorrect assessments or incorrect classifications being uncovered. Initially, there was an arrangement within the scope of the calculated pseudotime 81. Following a linking of the hidden label of cell A 21 to an expert-generated label of cell A 22, the hidden label of cell B 23 to an expert-generated label of cell B 24, the hidden label of cell C 25 to an expert-generated label of cell C 26, and the hidden label of cell D 27 to an expert-generated label of cell D 28, it is possible to initially establish an estimated class or development stage border 111. In the process, the hidden labels and the expert-generated labels are linked by means of directed edges 36. However, in the process, it was found that one expert-generated label 28 refers to a different class than the hidden label 27 associated therewith, which is younger in pseudotime. This indicates an assessment error of the expert 112.

The identified discrepancy with the presumed assessment error between the labels can subsequently be provided to the expert in form of feedback such that a reevaluation or verification is possible. Among other things, this renders an efficient assistance system for cell classification implementable.

EXAMPLES

Example 1

Pseudotime Inference

The pseudotime of a cell describes the developmental progress of the cell along a dynamic process such as cell differentiation. The greater the pseudotime of a cell, the more mature the cell is. Pseudotime inference algorithms can be used to create a pseudotemporal ordering for all cells in a population. Pseudotime inference algorithms are usually applied to single-cell gene expression similarity measurements (Haghverdi et al., 2016, Nature Methods, 13(10), 845-848), where adjacent cells have higher expression similarity. These algorithms can be applied to medical images by interpreting the pixels of a cell image as information in respect of this cell, similar to gene expression data, to obtain an ordering of the cells along trajectories. There are a multiplicity of pseudotime inference methods to date, which differ in terms of the requirement of existing prior information, scalability, and type of topology (Saelens et al., 2019, Nature Biotechnology, 37, 547-554). Most pseudotime inference methods consist of two parts. The first part is the calculation of a low-dimensional representation from the given expression data of the cells, and the second part is the ordering of the cells along an inferred trajectory. Here, use was made of the SCORPIUS (Cannoodt, 2016, SCORPIUS improves trajectory inference and identifies novel modules in dendritic cell development, bioRxiv:10.1101/079509v2) and STREAM (Chen et al., 2019, Nature Communications, 10, 1, 1903) algorithms. SCORPIUS shows very good performance for linear datasets, while STREAM is well-suited to datasets with tree-like topologies. Given the expression profiles of the cells, SCORPIUS obtains a low-dimensional representation using multi-dimensional scaling (MDS). Next, SCORPIUS applies k-means clustering and sets the initial trajectory by connecting the cluster centers. The final trajectory results from an iterative refinement through the principal curves algorithm. The pseudotime is calculated by projecting the low-dimensional representations onto the trajectory. Similarly, STREAM first determines relevant features and then performs dimensionality reduction using modified locally linear embedding (MLLE). In the new embedding, an implementation of elastic principal graphs (ElPiGraph) (Albergante et al., 2018, Robust and scalable learning of complex dataset topologies via ElPiGraph, arXiv:1809.07580v2) is used to infer the trajectory and branching points. ElPiGraph approximates datasets with complex topologies by minimizing the elastic energy of the embedding and applying graph transformations. The cells are then projected onto the resulting tree according to their pseudotimes and their assigned branches (see also Chen et al., 2019, Nature Communications, 10, 1, 1903).

Example 2

Hidden Markov Trees

Hidden Markov trees are used to describe the differentiation process of the cells, which is a stochastic process following the Markov assumption (Abkowitz et al., 1996, Nature Medicine, 2, 2, 190-197). There is one root cell type, and all other cell types develop therefrom and can be mapped onto a tree-like topology reflecting their respective progeny. Assuming that the topology of the dataset, i.e., the shape of the Markov tree, is known, the following applies:

Definition 1: A tree $\overline{ZT}$ is a Markov tree if for each leaf, the directed path connecting the root and the leaf is a Markov chain. A hidden Markov tree is an extension of a Markov tree, and it is used for applications where the Markov property does not hold or where the states can only be observed indirectly. The model consists of observed variables and hidden variables, where only the hidden variables follow the Markov property. The presently observed variable depends on the present hidden state, but neither on previous observed states nor on previous hidden states.

Define $\overline{ZT}:=(Z1, \ldots, ZT)$ and $\overline{XT}:=(X1, \ldots, XT)$, for T ∈ N, to be the hidden tree and the observed tree, respectively. The roots of the trees are Z1 and X1, and both trees have the same indexing structure.

Definition 2: Let $\overline{XT}$ and $\overline{ZT}$ be two trees, where X1 is the observed tree and $\overline{ZT}$ is the hidden tree. The pair $(\overline{ZT}, \overline{XT})$ is a hidden Markov tree (HMT) if (i) $\overline{ZT}$ is a Markov tree, and (ii) the distribution of the observed variable Xt depends only on the hidden variable Zt for all t∈{1, ..., T}.

For the application to cell image labels, the variable Xt corresponds to the noisy (observed) expert label, and Zt represents the true (unobservable) labels of the image, which may be different from the expert labels. The sequence of images is sorted by increasing pseudotime, which has been calculated before by a suitable pseudotime inference algorithm. Let K be the number of cell types and T be the number of images in the dataset.

Definition 3: The hidden Markov tree $(\overline{ZT}, \overline{XT})$ is governed by the parameters $n \in [0, 1]^K$, $A^{(t)} \in [0, 1]^{K \times K}$ and $B \in [0, 1]^{K \times K}$.

The following definitions apply for $2 \leq t \leq T$, $1 \leq k$, $\tilde{k} \leq K$:

$$\pi_k := \mathbb{P}(Z_1 = k),$$

$$A_{kl}^{(t)} := \mathbb{P}(Z_t = l | Z_{p(t)} = k),$$

$$B_{k\tilde{k}} := \mathbb{P}(X_t = \tilde{k} | Z_t = k),$$

where p(t) denotes the parent of node t.

π denotes the start probability, $A^{(t)}$ denotes the transition matrix at node t, and B denotes the emission matrix. If the transition matrix $A^{(t)}$ is independent of t, the model is called homogeneous; otherwise, the model is called inhomogeneous. The transition matrix $A^{(t)}$ describes the probability of staying in the present cell type or changing to a child cell type. The emission matrix B represents the expert labeling error model, where $B_{k\tilde{n}}$ is the probability that the expert predicts label $\tilde{k}$ when the true cell type of the cell in the image is k.

A hidden Markov model (HMM) is a special case of an HMT, where the underlying topology is a chain.

Time-Dependent Transition Matrices

The following information is used to set up the parametric transition matrices. The topology of the dataset is known, and following the Markov assumption of blood cell differentiation (Abkowitz et al., 1996, Nature Medicine, 2, 2, 190-197), it is only possible for a cell to stay in the same cell type or to transition to one of the child cell types. There is no way to skip one cell type or to go back to a previous cell type. Once one of the end stages is reached, there are no transitions anymore. Standard homogeneous HMMs/HMTs are based on the assumption that the transition between states is independent of t, which would correspond to cells sampled uniformly across the development trajectory. However, in practice, these samples (i.e., the labeled cells) are from arbitrary points on the development trajectory, which is reflected by large variation in pseudotime difference between neighboring cells. This difference directly affects the probability of a cell to transition to a different cell type: the larger the pseudotime difference between two cells, the greater is the likelihood for a transition (and the lower is the likelihood of the cell to remain in the same cell type). Consequently, the entries of the transition matrix at node t should not only depend on the cell type of the previous cell, but also on the time difference between the present cell and the previous cell. To model the dependency of the transition matrix on the pseudotime, the algorithms for HMMs and HMTs were extended to the inhomogeneous case and appropriate parametric transition matrices were derived.

The following definitions apply:

$y_t \in \mathbb{R} \geq 0$ as the pseudotime difference between cell t−1 and cell t, after they have been ordered by increasing pseudotime. To find reasonable entries for the transition matrices, the transition probabilities at node t are defined as follows:

$$A_{kl}^{(t)} = \mathbb{P}(Z_t = l | Z_{t-1} = k, y_t)$$

$$= \frac{\mathbb{P}(Z_t = l, Z_{t-1} = k, y_t)}{\mathbb{P}(Z_{t-1} = k, y_t)}$$

$$= \frac{\mathbb{P}(Z_{t-1} = k) \mathbb{P}(Z_t = l | Z_{t-1} = k) \mathbb{P}(y_t | Z_t = l, Z_{t-1} = k)}{\mathbb{P}(Z_{t-1} = k) \mathbb{P}(y_t | Z_{t-1} = k)}$$

$$= \frac{\mathbb{P}(Z_t = l | Z_{t-1} = k) \mathbb{P}(y_t | Z_t = l, Z_{t-1} = k)}{\mathbb{P}(y_t | Z_{t-1} = k)}.$$

Here, $P(Z_t=l|Z_{t-1}=k) =: p_{kl} \in [0, 1]$ is the transition probability from cell type k to cell type l. Let $p_{kl}$ be a constant independent of t, with condition $\sum_{l=1}^{k} p_{kl} = 1$ for all k.

The support of $y_t$ is known to be $[0, \infty)$ for the probability $P(y_t|Z_t=l, Z_{t-1}=k)$. Since there is no more information about the distribution of the pseudotime difference, the maximum entropy probability distribution is used. The least informative distribution for a random variable with support $[0, \infty)$ and mean $1/\lambda$ is the exponential distribution with rate $\lambda$. Let the rate $\lambda$ be dependent on the cell types k and l.

Then, for each possible transition in the cell lineage tree, the entry in the transition matrix after normalization has the form $$A_{kl}^{(t)} = \frac{p_{kl} \cdot \lambda_{kl} \exp(-\lambda_{kl} \cdot y_t)}{\sum_{i=1}^{K} p_{kl} \cdot \lambda_{kl} \exp(-\lambda_{kl} \cdot y_t)}$$

for $p_{kl} \in [0, 1]$ and $\lambda_{kl} > 0$.

The parameters in this formula are learned using the generalized EM algorithm (Neal and Hinton, 1998, A view of the EM algorithm that justifies incremental, sparse, and other variants, Learning in Graphical Models, 355-368) since the corresponding objective function is intractable.

The generalized Viterbi algorithm (Durand et al., 2004, IEEE Transactions on Signal Processing, 52(9), 2551-2560) then computes the most probable hidden variables arg max $_{Z1: T}$ P (Z1: T X1: T).

Example 3

The TIMELY Algorithm

TIMELY combines pseudotime inference methods with inhomogeneous HMTs. The pseudotime inference algorithm establishes an intrinsic ordering of the cells based on morphology, and the HMT then finds inconsistent labels and proposes correct labels of the cells corresponding to the true cell types. The input of TIMELY is a set of images together with noisy expert labels. First, a network (convolutional network) is used to learn meaningful feature representations of the cell images that are consistent with the morphology of the cells. The convolutional network consists of three convolutional layers with 32 filters each, where the filter size is 3×3. After each convolutional layer, there is a max-pooling layer with a pooling size of 2×2. A bottleneck of 50 units, which provides the resulting feature vectors, is followed by two dense layers with 30 hidden units each and an output layer.

As an alternative, unsupervised methods such as autoencoders were also explored to learn feature representations of the images so that the training is not affected by noisy labels. This yielded qualitatively similar findings.

Next, a suitable pseudotime inference method was applied to calculate the pseudotimes. The cells were ordered according to increasing pseudotime. SCORPIUS or STREAM was used, depending on the topology of the data. The sorted expert labels served as the observed information in the HMT, and the hidden labels are the true cell types to be determined. The background information about the dataset can be used to fix the start probabilities n and the emission matrix B, while the parameters of the transition matrices are learned by the generalized EM algorithm. Through the generalized Viterbi algorithm, the most probable true labels and the estimated cell type borders were found, which are unique due to the Markov assumption (Abkowitz et al., 1996, Nature Medicine, 2, 2, 190-197).

Any inconsistencies between the true labels and the expert labels are potential mistakes by the expert. Hematologists can reconsider the affected images and, if necessary, correct the labels of the cells. The method is summarized in Algorithm 1 (see below). TIMELY was implemented in Python, and the library SciPy is used for maximizing the objective function in the generalized EM algorithm.

Algorithm 1: TIMELY

Input: Images and noisy expert labels

Output: Images with inconsistent labels and proposed labels

1: Use background information about the dataset to define the topology of the HMT, the start probabilities n, and the emission matrix B.

2: Learn feature representations of the images using a neural network.

3: Choose a suitable pseudotime inference algorithm and calculate the pseudotimes on the basis of the feature vectors.

4: Sort the corresponding expert labels according to increasing pseudotime.

5: Set up an HMT, where the sorted expert labels are the observed information.

6: Learn the parameters in the transition matrices A(t) using the generalized EM algorithm.

7: Apply the generalized Viterbi algorithm to infer the most probable true labels.

8: Identify images with inconsistent labels by comparing the true labels with the expert labels.

Example 4

Baseline Methods

TIMELY was compared to three baseline methods. As explained above, most algorithms are robust to noisy data labels, find and remove noisy labels, or model label noise explicitly, but they do not propose new labels.

The algorithms k-nearest neighbors (k-NN) and k-nearest centroid neighbors (k-NCN) (Sanchez et al., 1997, Pattern Recognition Letters, 18, 11-13, 1179-1186) find neighbors for each instance for a given distance measure. A commonly used distance measure for k-NN is the Euclidean distance, while, for k-NCN, instances were added to the set of nearest neighbors for which the centroid of the new set is nearest to the considered instance. The label of the considered instance is then obtained by a majority vote. If the majority vote yields a different label than the original label of the instance, or if there is a tie, the instance might be incorrectly labeled.

To compare this method with other methods that also propose corrections, these two methods were extended with generalized editing (Koplowitz and Brown, 1981, Pattern Recognition, 13, 3, 251-255), i.e., numbers k and k' with $(k+1)/2 \leq k' \leq k$ were chosen for k-NN and k-NCN. For each instance, if there are at least k' nearest neighbors from a different cell type, the cell type of the instance is changed to that type. Unlike in Koplowitz and Brown, 1981, no samples were deleted. For both methods, k=3 and k'=2 were chosen, which are common values in the literature (Saez et al., 2015 Journal of Medical Informatics & Technologies, 24, pp. 123-130).

TIMELY was also compared to cleanlab (Northcutt et al., 2019, Confident learning: estimating uncertainty in dataset labels, arXiv:1911.00068v1), which is based on confident learning Northcutt et al., 2017, Learning with confident examples: rank pruning for robust classification with noisy labels, in Proceedings of the 33rd Conference on Uncertainty in Artificial Intelligence. AUAI Press) and finds labeling errors. It estimates the noise rates by calculating the joint distribution between noisy and uncorrupted labels and then prunes inconsistent samples.

Example 5

Simulation Data

Since expert labels from real-world datasets are often noisy, the ground truth labels of the images are unknown. For comparing the algorithm described herein to other methods in finding inconsistent labels, three datasets with different noise levels that mimic the cell differentiation setting were simulated. Each dataset consists of 250 samples from five cell types, where the underlying topology is a chain. The process of simulating the datasets is the following:

1. Let $X \in R^{2 \times 250}$, where X is normally distributed.
2. Sort the columns of X by increasing $X_{1j}$, $1 \leq j \leq 250$.
3. Define the corresponding ground truth labels $Y \in R^{250}$, where the entries $Y_{50(i-1)+1}:50$ are i for $i \in \{1 \ldots 5\}$.
4. Apply mapping P to project X to a higher-dimensional space with $\tilde{X} = PX \in R^{k \times 250}$. k=50 is chosen to be consistent with the real-world datasets.
5. Add noise level $l \in \{10, 20, 30\}$ to the ground truth labels Y by randomly changing l% of the entries in Y to different labels.

The steps 1 to 4 are repeated for each noise level.

The idea is that the samples have a low-dimensional ordering, corresponding to the pseudotemporal ordering, which can be retrieved by dimensionality reduction of the higher-dimensional feature vectors.

Example 6

Simulation Results

The results of the comparison is shown in Table 1. The methods k-NN+edit and k-NCN+edit modify the labels during application, while k-NN, k-NCN, and cleanlab only find possible labeling errors. TIMELY finds labeling errors and proposes new labels without changing them directly.

The proposed labels are compared with the ground truth labels to calculate the accuracy. The selected items are the instances that the algorithm marked as labeling errors. While TIMELY finds errors in a magnitude that is similar to the noise level, the other methods mostly find too many errors, without increasing the recall. Only in one case does k-NCN have a higher recall than TIMELY. The method according to the invention has the highest accuracy, precision, recall, and F1 score in all the other cases. Editing in k-NN and k-NCN often improves the F1 score compared to the versions without editing. However, editing of labels during application influences the classification of subsequent samples, and so the accuracy drops if there are too many false positives.

TABLE 1

Comparison to baseline methods for simulation data. TIMELY outperforms all baseline methods in terms of accurately identifying and correcting noisy labels.

| Noise level | Metric | TIME-LY | k – NN | k – NN + edit | k – NCN | k – NCN + edit | cleanlab |
|---|---|---|---|---|---|---|---|
| 10 | Accuracy | 0.984 | — | 0.920 | — | 0.944 | — |
|  | Selected items | 0.108 | 0.164 | 0.152 | 0.152 | 0.144 | 0.112 |
|  | Precision | 0.889 | 0.561 | 0.579 | 0.658 | 0.667 | 0.679 |
|  | Recall | 0.960 | 0.920 | 0.880 | 1.000 | 0.960 | 0.760 |
|  | F$_1$ Score | 0.923 | 0.697 | 0.698 | 0.794 | 0.787 | 0.717 |
| 20 | Accuracy | 0.992 | — | 0.932 | — | 0.820 | — |
|  | Selected items | 0.192 | 0.292 | 0.236 | 0.324 | 0.284 | 0.256 |
|  | Precision | 1.000 | 0.658 | 0.797 | 0.556 | 0.634 | 0.625 |
|  | Recall | 0.960 | 0.960 | 0.940 | 0.900 | 0.900 | 0.800 |
|  | F$_1$ Score | 0.980 | 0.781 | 0.863 | 0.687 | 0.744 | 0.702 |
| 30 | Accuracy | 0.972 | — | 0.792 | — | 0.712 | — |
|  | Selected items | 0.300 | 0.416 | 0.340 | 0.484 | 0.404 | 0.272 |
|  | Precision | 0.987 | 0.673 | 0.706 | 0.537 | 0.604 | 0.809 |
|  | Recall | 0.987 | 0.933 | 0.800 | 0.867 | 0.813 | 0.733 |
|  | F$_1$ Score | 0.987 | 0.782 | 0.750 | 0.663 | 0.693 | 0.769 |

Example 7

Application to Real Data

TIMELY was applied to two image datasets of stained white blood cells. All images were generated by a digital microscope (Cellavision, Siemens Healthineers AG) and labeled by an expert. Due to the challenges in manual labeling described above, the labels are noisy and partly incorrect. For the preparation of the images, a thin blood film was applied on a glass slide and stained. A digital microscope then located the blood cells and created corresponding images. The datasets contained images from a plurality of patients. TIMELY was applied to the whole dataset to first find the ordering of the images. Then, it suggested a label for each image. For a new patient, images from the same developmental tree can be mapped onto the already calculated tree, and consistent labels can be read off the tree directly by making use of the already computed transition borders.

Cell Lineage

Datasets

The first dataset consisted of 1000 cell images that contained five cell types of the granulopoiesis development line. The topology was a linear chain. There were 200 images, labeled by an expert as belonging to each of the cell types promyelocyte (PMY), myelocyte (MY), metamyelocyte (MMY), band neutrophil (BNE), and segmented neutrophil (SNE).

Parameters in HMM

Available background knowledge about the dataset was used to fix the start probabilities n and the emission matrix B. The dataset has five cell types, and the root type in the development process is known to be PMY. Thus, the start probabilities could be fixed as follows:

$\pi := (0.9\ 0.025\ 0.025\ 0.025\ 0.025)^T$

The first cell should be in the first cell type with high probability and in the other cell types with low probability.

The constant emission matrix B is based on estimations of an expert who could realistically estimate the probability of labeling errors. The emission matrix for the first dataset is as follows:

|     | PMY   | MY    | MMY   | BNE   | SNE   |
|-----|-------|-------|-------|-------|-------|
| PMY | 0.7   | 0.25  | 0.04  | 0.005 | 0.005 |
| MY  | 0.23  | 0.52  | 0.24  | 0.005 | 0.005 |
| MMY | 0.03  | 0.17  | 0.75  | 0.045 | 0.005 |
| BNE | 0.005 | 0.005 | 0.03  | 0.82  | 0.14  |
| SNE | 0.005 | 0.005 | 0.005 | 0.065 | 0.92  |

The more mature cell types band neutrophil and segmented neutrophil are fairly easy for humans to differentiate, while the first three cell types, especially myelocytes, are more difficult to label.

Pseudotime Inference

The SCORPIUS algorithm was used to compute the pseudotimes. Diffusion maps (Coifman and Lafon, 2006, Applied and Computational Harmonic Analysis, 21(1), 5-30) for dimensionality reduction were used before SCORPIUS was applied. Subsequently, SCORPIUS directly inferred the trajectory without performing MDS.

Visualization Tools

Following the parameter optimization, the HMM found unique transition borders between the cell types. A visualization tool for viewing the images was provided (see also FIG. 8). The images are ordered according to the inferred pseudotime. Each image corresponds to one point that is highlighted according to the expert label. The inferred transition borders from the HMM were integrated, and the interstices between the borders were labeled according to the proposed cell types. Inconsistent classifications could be identified by non-corresponding labels. The expert can click on each point to display the corresponding image and navigate to neighboring cells by clicking on the arrows. From this, they gain insight as to why a specific cell was marked as having an inconsistent label.

Inconsistent Labels

The percentage of consistent labels, where the hidden labels and expert labels coincide, is 72% according to the HMM. This means that there are 280 images with potentially wrong labels. By way of a confusion matrix, it was possible to show that the consistency is particularly low for myelocytes and metamyelocytes. Overall, the tendency of the values was similar to the expert's estimation of the emission matrix, as shown above.

Experiments have shown that the results are quite robust with respect to the emission matrix, and so small changes in the estimations will not significantly affect the results.

The 280 inconsistent images were passed to an expert for reclassification. For 128 of these images (45.7%), the expert confirmed the previous labels. For the remaining 152 cells, the expert either relabeled them as the cell types proposed by the HMM, or they could not assign a label with high confidence, meaning that up to 54.3% of the inconsistent images might have wrong labels. Most of the reclassifications related to the first three cell types in the development line, where changes in the morphology can be very subtle.

Cell Lineage Trees

Dataset

The second dataset consisted of 1821 cell images in ten classes, which are part of a development process with branching points. There were 200 images labeled by an expert as belonging to each of the promyelocyte (PMY), myelocyte (MY), metamyelocyte (MMY), band neutrophil (BNE), segmented neutrophil (SNE), blast (BL), basophil (BA), eosinophil (EO), and lymphocyte (LY) cell types. There were only 21 images for the last class plasma cell (PC). Eosinophils and basophils also have myelocytes, metamyelocytes, and band neutrophils as precursors. However, these exhibit different staining behavior than the precursors of the segmented neutrophils. Because those cell types are quite rare in the blood, they were not included in the dataset.

Parameters in HMT

The root cell should be a blast cell so that the entry for blast is very high in π. The constant emission matrix B is again based on discussions with an expert and is a consistent extension of the emission matrix shown above. The five additional cell types should not be too difficult to differentiate from the cell types of the first dataset because they are part of different development lines. Only the blasts have some similarities to the promyelocytes, which are descendants of the blasts. The end stages of segmented neutrophil, basophil, and eosinophil should be easy for experts to classify.

Pseudotime Inference

The STREAM algorithm was used to infer a reasonable tree for the dataset. Two of the three possible branching points matched the branching points from the cell lineage tree. However, the last branching point, where the eosinophils branch off from the metamyelocytes, is different. In general, the eosinophils are far away from the other cell types in the feature space following the dimensionality reduction. The connection point to the remaining tree might not be correct. A further reason could be that the precursor cells of segmented neutrophils and eosinophils look alike. Eosinophils have the same progenitor stages as the neutrophils, which are only stained in a different color. The algorithm might also identify the metamyelocytes as a previous development stage of the eosinophils. The range of the pseudotimes is still plausible for all cell types however.

Inconsistent Labels

The percentage of consistent labels according to the HMT is 69%, meaning that there are 564 images with potentially wrong labels. The blasts and promyelocytes seem to be mixed up often, while basophils and eosinophils have high agreement between hidden labels and expert labels, presumably on account of their distinct staining colors. The agreement for lymphocytes is also very high since cells from different development lines are usually easier to differentiate.

The 564 inconsistent images were given to an expert for reclassification. The expert confirmed their previous labels for 341 images, and so up to 40.1% of the inconsistent images might have wrong labels. Most reclassifications affected promyelocytes, myelocytes, and metamyelocytes, which represent the first three cell types in the granulopoiesis line. The cells were mostly classified as the progenitor of the cell type determined by the experts.

Summary of the Results

As a method according to the invention, TIMELY, a human-centered approach for increasing labeling consistency within the scope of medical imaging for cell type classification, was introduced.

TIMELY takes as input cell microscopy images together with noisy expert-generated labels, identifies inconsistent labels and proposes alternative, consistent labels on the basis of a two-step procedure.

In the first step, TIMELY establishes an intrinsic order between cells with the aid of a pseudotime inference algorithm. In the second step, TIMELY creates a Markov model on the basis of the ordered cells and their noisy labels. An HMM or an HMT is used, depending on the complexity of the topology of the dataset. Pseudotime estimations are combined with interpretable HMTs in order to establish a system that assists an annotating hematologist or histologist, for example, with generating more consistent cell classifications. By sorting the cells according to the pseudotime, the annotating hematologist or histologist is able to consider each cell in the neighborhood of cells that have a similar morphology. This assists them in making more consistent decisions. Moreover knowledge in the art is transparently and explicitly encoded in form of differentiation hierarchies, start probabilities (see above), and an expert-driven emission matrix (see above), reflecting prior experience on the likelihood of labeling errors.

Taken together, this allows, for example, a hematologist or histologist to develop an intuitive understanding as to why specific cells are suggested as being inconsistently labeled and helps an easier adoption in practice.

Manually labeling cells is also a time-consuming process, and the method according to the invention can be applied to reduce the time experts spend on this task.

As soon as the parameters of an HMT are optimized, new images from the same developmental tree can be mapped onto the already calculated tree, and consistent labels can be read directly off the tree by virtue of making use of the already computed transition borders.

An additional, exemplary use case of TIMELY is the application to automatically generated labels since they are often noisy. Moreover, the classification algorithm does not include all possible cell types. These labels would then serve as the observed information of the HMT, and only the inconsistent labels will be given to the expert for reclassification.

REFERENCE SIGNS

1 Image data
2 Expert-generated labels
3 Feature calculation
4 Machine learning
5 Classification model
11 Calculation of the similarity graph
12 Creation of a probabilistic model in the form of a conditional random field (CRF)
13 Inference of hidden labels
14 Correction of the hidden labels
21 Hidden label of cell A
22 Expert-generated label of cell A
23 Hidden label of cell B
24 Expert-generated label of cell B
25 Hidden label of cell C
26 Expert-generated label of cell C
27 Hidden label of cell D
28 Expert-generated label of cell D
29 Hidden label of cell E
30 Expert-generated label of cell E
31 Hidden label of cell F
32 Expert-generated label of cell F
33 Hidden label of cell G
34 Expert-generated label of cell G
35 Linking of the hidden labels among themselves
36 Linking of the hidden labels and the expert-generated labels
41 Transition of cell development stages
42 Myeloblast
43 Promyelocyte
44 Myelocyte
45 Metamyelocyte
46 Band segmented neutrophil
51 Calculating the pseudotime
52 Creating a probabilistic model in the form of a hidden Markov model (HMM)
53 Inferring label borders in pseudotime
61 Convolution
62 Max pooling
63 Compression
64 Representation in the feature space
71 Transformation
72 Feature space
73 Cells within the scope of their development in the feature space
81 Cells in pseudotime
91 Distance to the next cell in pseudotime
101 Coding in the emission probability of the HMM
102 Coding by the transition matrix of the HMM
111 Estimated class or development stage border
112 Error by the expert

The invention claimed is:

1. A computer implemented method using a trained probabilistic graphical model to adapt hidden labels within the scope of medical image processing of cells, the trained probabilistic graphical model stored in a memory and executable on a processor, the method including the steps of: providing hidden labels based on similarities between at least two data points of images as training data and expert-generated labels associated with this training data, the images comprising image information of respectively one cell; linking the hidden labels and the expert-generated labels, the linking comprising a connecting of all hidden labels among themselves and a connecting of each hidden label to a respective expert-generated label; and adapting or confirming the hidden labels based on the trained probabilistic graphical model, the adapting or confirming including linking an adapted or confirmed hidden label with an image of a cell and storing in the memory the image of the cell together with the linked adapted or confirmed hidden label.

2. A computer-implemented method for producing the trained probabilistic graphical model of claim 1 for verifying or improving a consistency of labels within a scope of medical image processing, the method including the following steps: providing a set of images as training data, the images comprising image information of respectively one cell; calculating a feature space for the training data with the aid of a deep convolutional neural network (DCNN) executing on a processor, with an image corresponding to a feature vector in the feature space; calculating similarities between at least two data points of the training data based on the feature space; providing expert-generated labels for cells, the images of which were provided as training data; calculating the hidden labels based on similarities between at least two data points of the training data and the expert-generated labels; and producing a conditional random field (CRF) model as the trained probabilistic graphical model.

3. A non-transitory computer program product with a computer program, which is directly loadable into a memory device of a computer, comprising program sections for carrying out all steps of a method as claimed in claim 2 when the computer program is executed on the computer.

4. The computer-implemented method as claimed in claim 2, wherein the calculation of the similarities between at least two data points comprises creation of a similarity graph.

5. A data processing apparatus, embodied to verify or improve a consistency of labels within a scope of medical image processing, wherein the apparatus has at least one processor and a memory, wherein the at least one processor is configured to load and execute program code from the memory and, in response to execution of the program code, carry out the following steps:
providing an image of a cell;
providing an available expert-generated label for this image;
calculating a feature space for the image;
applying the method as claimed in claim 1 and the trained probabilistic graphical model of claim 1 on the calculated features of the image;
linking a label to the image, the linking comprising a correction or confirmation of the already available expert-generated label for this image; and
outputting or storing the image together with the corrected or confirmed linked label.

6. The computer-implemented method as claimed in claim 1, wherein the adapted or confirmed hidden labels, which were obtained based on the probabilistic graphical model as claimed in claim 1, are used to repeat the method as claimed in claim 1.

7. The computer-implemented method as claimed in claim 1, wherein the linking of the calculated label and the expert-generated label is carried out based on a conditional probability of the correctness of the expert-generated label.

8. A computer-implemented method for producing a trained probabilistic graphical model for verifying or improving a consistency of labels within a scope of medical image processing, wherein a cell can represent different development stages of the cell, comprising the following steps: providing a set of images as training data, the images comprising image information of respectively one cell; calculating a feature space for the training data with the aid of a deep convolutional neural network (DCNN), with an image corresponding to a feature vector in the feature space; calculating similarities between at least two data points of the training data based on the feature space; calculating a pseudotime, which orders the at least two data points as per a development sequence; providing expert-generated labels for cells whose images were provided as training data; calculating hidden labels based on the development sequence reflected in the pseudotime and the expert-generated labels; and producing and storing in a memory a probabilistic graphical model for adapting the hidden labels, the probabilistic model being a hidden Markov model (HMM) in the case of a linear development sequence and a hidden Markov tree (HMT) in the case of a dichotomous development sequence.

9. A computer-implemented method, wherein the probabilistic graphical model of claim 8 is used to adapt hidden labels within the scope of medical image processing of cells, which can represent different cell development stages, including the steps of:
providing hidden labels based on similarities between at least two data points of a set of images as training data, the images comprising image information of respectively one cell, and a pseudotime inferred therefrom, and expert-generated labels associated with the training data;
linking the hidden labels and the expert-generated labels, the linking comprising a connection of all labels by way of directed edges; and
adapting or confirming the hidden labels based on the probabilistic graphical model.

10. The computer-implemented method as claimed in claim 9, wherein the adapted or confirmed hidden labels, which were obtained based on the probabilistic graphical model as claimed in claim 9, are used to repeat the method as claimed in claim 9.

11. The computer-implemented method as claimed in 9, wherein the linking of the calculated label and the expert-generated label is carried out based on a conditional probability of the correctness of the expert-generated label.

12. The computer-implemented method as claimed in claim 8, wherein the calculation of the similarities between at least two data points comprises creation of a similarity graph.

13. A non-transitory computer-readable medium, on which program sections that are readable and executable by a computer are stored in order to carry out all steps of the method as claimed in claim 8 when the program sections are executed by the computer.

14. A data processing apparatus for adapting hidden labels within a scope of medical image processing of cells based on a trained probabilistic graphical model, comprising: a first unit for (i) providing hidden labels based on similarities between at least two data points of a set of images as training data and expert-generated labels associated with this training data, the images comprising image information of respectively one cell, or (ii) providing hidden labels based on similarities between at least two data points of a set of images as training data, the images comprising image information of respectively one cell, and a pseudotime inferred therefrom, and expert-generated labels associated with the training data; a second unit for (i) linking the hidden labels and the expert-generated labels, the linking comprising a connecting of all hidden labels among themselves and a connecting of each hidden label to a respective expert-generated label, or (ii) linking the hidden labels and the expert-generated labels, the linking comprising connecting each hidden label to a respective expert-generated label; and a third unit for receiving adapted hidden labels based on the probabilistic graphical model.

15. A computer-implemented method for verifying or improving a consistency of labels within a scope of medical image processing, including the steps of: providing an image of a cell to a first processor; providing an available expert-generated label to the first processor; using background information in respect of the image of the cell to define a topology of a hidden Markov tree (HMT), a start probability, and an emission matrix; learning the feature representations of the image using a neural network executing on a first processor; choosing a suitable pseudotime inference algorithm and calculating pseudotimes based on feature vectors; sorting the available expert-generated labels according to increasing pseudotime; configuring the hidden Markov tree (HMT), in which the sorted expert-generated labels are observed information; learning parameters of transition matrices using a generalized EM (Expectation-Maximization) algorithm executing on the first or another processor; applying a generalized Viterbi algorithm in order to infer most probable true labels, the Viterbi algorithm executing on the first or another processor; identifying images with inconsistent labels by virtue of comparing actual the true labels with the expert-generated labels using the first or another processor; and outputting and storing in a memory images with inconsistent labels, which additionally contain proposed labels.

16. The computer-implemented method as claimed in claim 15, wherein a correction of an already available expert-generated label leads to a feedback query with an expert in respect of a labeling discrepancy.

\* \* \* \* \*